(12) United States Patent  
Grodzki et al.

(10) Patent No.: US 12,178,562 B2  
(45) Date of Patent: Dec. 31, 2024

(54) METHOD FOR PERFORMING A MAGNETIC RESONANCE MEASUREMENT OF A PATIENT, MAGNETIC RESONANCE APPARATUS, AND COMPUTER PROGRAM PRODUCT

(71) Applicant: Siemens Healthcare GmbH, Erlangen (DE)

(72) Inventors: David Grodzki, Erlangen (DE); Dieter Ritter, Fürth (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 17/697,890

(22) Filed: Mar. 17, 2022

(65) Prior Publication Data

US 2022/0296119 A1 Sep. 22, 2022

(30) Foreign Application Priority Data

Mar. 18, 2021 (DE) ...................... 10 2021 202 670.2

(51) Int. Cl.
*G01R 33/54* (2006.01)
*A61B 5/055* (2006.01)
(Continued)

(52) U.S. Cl.
CPC ............ *A61B 5/055* (2013.01); *G01R 33/543* (2013.01); *G01R 33/56563* (2013.01);
(Continued)

(58) Field of Classification Search
CPC . A61B 5/055; A61B 5/7285; A61B 2090/374; A61B 5/1102; A61B 5/113; A61B 5/1113; G01R 33/543; G01R 33/56563; G01R 33/5673; G01R 33/243; G01R 33/5676; G01R 33/5607; G01R 33/56509; G06T 7/0012; G06T 2207/10088
See application file for complete search history.

(56) References Cited

U.S. PATENT DOCUMENTS

2014/0292333 A1\* 10/2014 Beck .................... G01R 33/243  
324/309  
2015/0309147 A1 10/2015 Schmitter et al.  
(Continued)

*Primary Examiner* — Rishi R Patel  
(74) *Attorney, Agent, or Firm* — Lempia Summerfield Katz LLC

(57) ABSTRACT

A method for performing a magnetic resonance measurement of a patient using a magnetic resonance apparatus is provided. The magnetic resonance apparatus includes a radiofrequency antenna unit for producing an excitation pulse. A first B0 field map for a first motion state of the patient, and a second B0 field map for a second motion state of the patient are provided. A first excitation pulse for the first motion state, and a second excitation pulse for the second motion state are determined based on the first B0 field map and the second B0 field map. A magnetic resonance measurement is performed, during which the motion state of the patient is monitored. When the patient is in the first motion state, the radiofrequency antenna unit transmits the first excitation pulse. When the patient is in the second motion state, the radiofrequency antenna unit transmits the second excitation pulse.

16 Claims, 4 Drawing Sheets

(51) Int. Cl.
*G01R 33/24* (2006.01)
*G01R 33/565* (2006.01)
*G01R 33/567* (2006.01)
*G06T 7/00* (2017.01)
*A61B 5/00* (2006.01)
*A61B 90/00* (2016.01)

(52) U.S. Cl.
CPC ........ *G01R 33/5673* (2013.01); *G06T 7/0012* (2013.01); *A61B 5/7285* (2013.01); *A61B 2090/374* (2016.02); *G01R 33/243* (2013.01); *G01R 33/5676* (2013.01); *G06T 2207/10088* (2013.01)

(56) References Cited

U.S. PATENT DOCUMENTS

| | | | |
|---|---|---|---|
| 2016/0169997 A1* | 6/2016 | Fautz | G01R 33/543 324/309 |
| 2018/0353139 A1 | 12/2018 | Speier | |
| 2021/0278492 A1 | 9/2021 | Grodzki et al. | |
| 2022/0244329 A1* | 8/2022 | Liebig | G01R 33/5659 |

* cited by examiner

METHOD FOR PERFORMING A MAGNETIC RESONANCE MEASUREMENT OF A PATIENT, MAGNETIC RESONANCE APPARATUS, AND COMPUTER PROGRAM PRODUCT

This application claims the benefit of German Patent Application No. DE 10 2021 202 670.2, filed on Mar. 18, 2021, which is hereby incorporated by reference in its entirety.

BACKGROUND

The present embodiments relate to a method for performing a magnetic resonance measurement of a patient, to a magnetic resonance apparatus, and to a computer program product.

In medical technology, high soft-tissue contrasts are a particular feature of imaging using magnetic resonance (MR), also known as magnetic resonance imaging (MRI). In this process, a human or animal patient is typically positioned in an examination space of a magnetic resonance apparatus. During a magnetic resonance measurement, radiofrequency (RF) transmit pulses (e.g., excitation pulses) are usually radiated into the object under examination by a radiofrequency antenna unit of a magnetic resonance apparatus. The excitation pulses produce an alternating magnetic field, known as a B1 field, in the examination space. This is distinct from a static magnetic field, otherwise known as a B0 field. In addition, a gradient coil unit of the magnetic resonance apparatus is used to switch gradient pulses, which produce magnetic field gradients (e.g., temporary magnetic field gradients) in the examination space. The transmit pulses that are produced excite nuclear spins in the patient, thereby actuating spatially encoded magnetic resonance signals. The magnetic resonance signals are received by the magnetic resonance apparatus and used to reconstruct magnetic resonance images.

The quality of the magnetic resonance images is usually heavily dependent on the homogeneity of the magnetic field for aligning the nuclear spins. It is known to use shim coils to improve the homogeneity of the static magnetic field, and to take into account dynamic effects of eddy currents when configuring the gradient pulses. In addition, the quality of the magnetic resonance images may be impaired by motion artifacts.

SUMMARY AND DESCRIPTION

The scope of the present invention is defined solely by the appended claims and is not affected to any degree by the statements within this summary.

The present embodiments may obviate one or more of the drawbacks or limitations in the related art. For example, imaging in a magnetic resonance apparatus made better, such that fewer artifacts arise as a result of a movement of the patient.

A method includes performing a magnetic resonance measurement of a patient using a magnetic resonance apparatus. The magnetic resonance apparatus has a radiofrequency antenna unit for producing an excitation pulse (e.g., for producing an alternating magnetic field). A first B0 field map for a first motion state of the patient, and at least one further B0 field map (e.g., a second B0 field map) for at least one further motion state (e.g., a second motion state) of the patient are provided. A first excitation pulse for the first motion state and at least one further excitation pulse (e.g., a second excitation pulse) for the at least one further motion state (e.g., the second motion state) are determined (e.g., by a system control unit of the magnetic resonance apparatus) based on the first B0 field map and the at least one further B0 field map (e.g., the second B0 field map). In addition, a magnetic resonance measurement is performed, during which the motion state of the patient is monitored. When the patient is in the first motion state, the radiofrequency antenna unit transmits the first excitation pulse. When the patient is in the at least one further motion state (e.g., the second motion state), the radiofrequency antenna unit transmits the at least one further excitation pulse (e.g., the second excitation pulse). This does not provide that the first or the at least one further (e.g., second) excitation pulse is to be transmitted whenever the patient is in the first motion state or the second motion state, respectively.

In the further description, the term "second" is generally used instead of "at least one further" for the sake of simplicity. For example, in the further description, for the sake of simplicity, "second B0 field map" is used instead of "at least one further B0 field map", "second motion state" is used instead of "at least one further motion state", and "second excitation pulse" is used instead of "at least one further excitation pulse". The method is obviously not limited to specific excitation pulses being determined and transmitted only for two motion states. Thus, an excitation pulse is determined and transmitted not just for each of exactly two motion states but for each of at least two excitation states. Advantages and attributes that relate to the first excitation pulse and/or the second excitation pulse may also be transferred to further excitation pulses. For example, the method may further include that in addition to the first B0 field map and the second B0 field map, at least one further B0 field map is provided for at least one further motion state of the patient. At least one further excitation pulse may be determined for the at least one further motion state, with the at least one further excitation pulse being transmitted when the patient is in the at least one further motion state.

The method may therefore include, for example, providing at least two B0 field maps (e.g., the first B0 field map and the second B0 field map), each for one motion state of the patient. An excitation pulse (e.g., the first excitation pulse and the second excitation pulse) is determined for each motion state (e.g., for the first motion state and the second motion state) based on the acquired at least two B0 field maps. The magnetic resonance measurement, during which the motion state of the patient is monitored, is performed. The radiofrequency antenna unit transmits the relevant excitation pulse when the patient is in the associated motion state.

The magnetic resonance apparatus may also have a main magnet for producing a static magnetic field, and a gradient coil unit for producing magnetic field gradients.

The first excitation pulse and/or the second excitation pulse may produce magnetic resonance signals that are received by the magnetic resonance apparatus (e.g., by the radiofrequency antenna unit of the magnetic resonance apparatus). The radiofrequency antenna unit may include, for this purpose, for example, one or more local coils and/or a body coil that is fixedly integrated in the magnetic resonance apparatus. One or more magnetic resonance images may be produced from the received magnetic resonance data (e.g., by a system control unit of the magnetic resonance apparatus). The magnetic resonance images are suitable for medical diagnostics, for example.

The first B0 field map and/or the second B0 field map may be produced using acquired measurement data and/or simulation.

For example, the system control unit of the magnetic resonance apparatus determines one B0 field map at a time from acquired measurement data. In one embodiment, the first B0 field map is acquired at at least one first time instant, and the second B0 field map is acquired at at least one second time instant. The patient is in a first motion state at the at least first time instant, and the patient is in a second motion state at the at least one second time instant. The first motion state and the second motion state usually differ. A "time instant" may also include a short time interval (e.g., one second), in which at least a portion of the B0 field map (e.g., of the measurement data for a B0 field map) is acquired.

For example, a portion of a B0 field map (e.g., of the measurement data for a B0 field map) is acquired at each time instant of a plurality of time instants. This may be the case, for example, when a single time instant is not sufficiently long to record the measurement data needed for a B0 field map. The acquisition may be performed, for example, by a triggered or gated measurement.

For example, a portion of the first B0 field map (e.g., of the measurement data for the first B0 field map) is acquired at each first time instant of a plurality of first time instants. For example, a portion of the second B0 field map (e.g., of the measurement data for the first B0 field map) is acquired at each time instant of a plurality of second time instants.

For example, at least one further B0 field map may be acquired at at least one further time instant. The patient is in at least one further motion state that differs from the first motion state and the second motion states, at the at least one further time instant.

The method may therefore include, for example, acquiring at least two B0 field maps (e.g., the first B0 field map and the second B0 field map), each at a different time instant (e.g., the first time instant and the second time instant). The patient is in different motion states at the time instants.

In one embodiment, a B0 field map (e.g., the first B0 field map and/or the second B0 field map) is produced by simulation. For example, the first B0 field map may be produced using acquired measurement data, and the second B0 field map may be simulated based on the first B0 field map (e.g., taking into account the first motion state and the second motion state).

The first B0 field map and/or the second B0 field map may be determined according to patient-induced B0 deviations. For example, parameters of the patient such as height, weight, and/or position may be used to model in an automatic calculation by the controller, or to retrieve from a database, the effects thereof on the homogeneous B0 field. The B0 field maps determined in this manner make it possible to use the excitation pulses (e.g., spectrally selective excitation pulses) to correct the effects of these B0 variations caused by the patient, and, for example, to improve in the produced image the suppression of fat by fat saturation.

A B0 field map may describe a spatial variation in the B0 field in the acquisition region of the magnetic resonance apparatus. For example, in contrast with the B1 field, a magnetic field that varies over time only at frequencies lying far below the Larmor frequency (e.g., by a factor of 10, 50, or more) is considered to be a B0 field. For example, the B0 field may be a static main magnetic field produced by the main magnet of the magnetic resonance apparatus. The B0 field map may be stored, for example, in a memory of the system control unit.

For example, a nuclear-spin excitation to be achieved (e.g., in a volume under examination) is specified, for example, by the system control unit. This depends, for example, on a magnetic resonance sequence used during the magnetic resonance measurement. For example, a desired flip angle of the nuclear spins (e.g., 90 degrees or 180 degrees) is specified. The excitation, for example, may involve selective excitation of certain nuclei (e.g., certain nuclei of atoms in specific bonds that have different Larmor frequencies).

In one embodiment, the first excitation pulse and/or the second excitation pulse for emission by the radiofrequency antenna unit are determined (e.g., by the system control unit). The excitation pulses are configured to achieve a predefined excitation. This may be, for example, that the excitation of the nuclear spins to be excited deviates from the excitation to be achieved by less than 10%, 5%, 1%, or 0.1% in a volume to be captured (e.g., in a slice to be imaged in the body of the patient). The determination of the first excitation pulse and the second excitation pulse takes into account, for example, the first B0 field map and the second B0 field map, and also possibly gradient fields present in the volume to be captured.

The gradient fields may also be regarded as a component of the B0 field and be contained in the B0 field map. For example, an optimization method such as least squares regression (LSR) or a method for minimum squared deviation) may be used to determine the spin excitation as a function of the B0 field map using Bloch equations and to minimize deviations from the defined excitation until the deviations lie below a predefined deviation. In one embodiment, for example, parameterized stored templates for excitation pulses, for which the parameters are optimized, or tables containing predefined excitation pulses, in which one having a minimum deviation is selected, are provided.

In one embodiment, the first excitation pulse and the second excitation pulse are each a spectrally selective excitation pulse configured, for example, to achieve saturation of the nuclear spins in the patient as the excitation to be achieved.

"Spectrally selective" may be, for example, that the relevant excitation pulse, as a result of different Larmor frequencies of the nuclear spins (e.g., caused by different nuclei), although, for example, caused by identical nuclei in different chemical bonds, excites the different types of nuclear spins or bond types in a predefined manner (e.g., causes a predefined change in the alignment of the nuclear spins in the B0 magnetic field). For example, it may be provided that nuclear spins in one bond type adopt, as a result of the spectrally selective excitation pulse, an alignment completely opposite to the direction of the magnetic field, or a flip angle of 90 degrees, whereas the nuclear spins in another bond type experience no change in alignment. The Larmor frequency may vary as a result of the different bonds by less than 100 parts per thousand, 50 parts per thousand, 10 parts per thousand, 5 parts per thousand, or 1 part per thousand.

The first excitation pulse and/or the second excitation pulse may be configured to achieve, as the excitation to be achieved, saturation of nuclear spins of a first bond type in the volume under examination. A predefined flip angle for the saturation may vary depending on the magnetic resonance sequence during performance of the magnetic resonance measurement (e.g., may equal the value 90 degrees or 180 degrees), with tolerances of, for example, up to +−10 degrees or +−20 degrees also being allowed. Saturation of the nuclear spins is considered to be, for example, the case when, for example, more than 80%, 90%, 95%, or 99% of the nuclear spins of the first bond type occupy the predefined flip angle or are in the tolerance range around the flip angle.

Saturation of the nuclear spins of a defined nucleus type or of a defined bond type by excitation pulses (e.g., saturation pulses) may be suitable for hiding fat in the image, for example. The technique is often marred, however, by B0 field variations (e.g., caused by different tissue boundaries of different permeability). A spectrally selective excitation pulse as the saturation pulse may present an opportunity for improving the image quality when employing suppression by saturation.

The first excitation pulse and/or the second excitation pulse may be configured to achieve different predefined target magnetizations for nuclear spins having at least two predefined different Larmor frequencies. By adjusting the amplitude for different frequency components of the spectrally selective excitation pulse (e.g., of the spectral energy distribution), predefined target magnetizations or flip angles may be set specifically for nuclear spins that have different Larmor frequencies (e.g., have different first and second chemical bonds). A simple example is a saturation pulse, for which, as before, saturation is set for a first bond type, whereas no change in the flip angle results for the other, second bond type. In one embodiment, the flip angles of both bond types may be altered simultaneously by different amounts, so as to accelerate the method and/or reduce the SAR exposure advantageously.

The excitation achieved by the first excitation pulse and/or the second excitation pulse may cause spatially homogeneous fat saturation. Body fat is frequently a disruptive substance in magnetic resonance images because body fat also has a high proton density and is often spatially tightly intertwined with other organs under examination. The slightly different nuclear spin of the protons in the chemical bonds of the hydrocarbons compared with water provides that, in principle, fat may be suppressed well by saturation pulses. As a result of the small frequency differences in the Larmor frequency, however, even small magnetic field variations, such as those caused dynamically by eddy currents, lead to poor image quality.

During performance of the magnetic resonance measurement, the system control unit, for example, outputs, via the radiofrequency antenna unit in accordance with a magnetic resonance sequence, the first excitation pulse or the second excitation pulse depending on the motion state of the patient. To output in accordance with the magnetic resonance sequence may be, for example, that the excitation pulse is transmitted at a predefined time instant as specified by the magnetic resonance sequence. This may include, for example, an output that is predefined in time in relation to gradient fields.

The first excitation pulse and/or the second excitation pulse may be suitable for taking account of, and/or correcting for, spatial variations in the B0 field. It is thereby possible to improve the quality of the magnetic resonance signals produced by the excitation pulses and of any magnetic resonance images reconstructed therefrom. In addition, it is possible to reduce the effort involved in possible correction and/or prevention of B0-field deviations (e.g., by active or passive shimming) and/or to lower the electromagnetic exposure for the patient.

The method may also include providing a first B1 field map for a first motion state of the patient, and a second B1 field map for a second motion state of the patient. For example, the method includes acquiring at least a first B1 field map at the first time instant and a second B1 field map at the second time instant. The first excitation pulse and the second excitation pulse are also determined based on, for example, the first B1 field map and the second B1 field map. For example, spectrally selective excitation pulses are determined as a function of the B1 field map.

The B1 field map may indicate, for example, variations in the amplitude of the radiofrequency magnetic B1 alternating field that is produced on the emission of an excitation pulse by the radiofrequency antenna unit. The variations may be caused, for example, by the geometry of the radiofrequency antenna unit or by the interaction with the patient (e.g., attenuation or absorption in the body). A B1 field map may be acquired with the patient, for example, by phase-sensitive mapping or by the Bloch-Siegert shift.

When determining the first excitation pulse and the second excitation pulse based on the first B1 field map and the second B1 field map, it is possible, for example, to compensate for an amplitude of the B1 field. The amplitude is detected in the associated B1 field map and is locally reduced in a region, by a higher amplitude of the excitation signal in this region (e.g., if the radiofrequency antenna unit has a plurality of channels) and/or by a longer duration of the excitation signal. If, for example, the region of the B1-field variation as a result of magnetic field gradients or B0-field variations correlates spatially with a different B0 field, it is possible, as a result of different Larmor frequencies, also to use a variation in the amplitude for corresponding spectral components of the excitation pulse for spatial homogenization of the excitation by the excitation pulse. Hence, the first excitation pulse and/or the second excitation pulse may also be used to reduce an inhomogeneity caused by B1 variation in magnetic resonance images to be produced.

In one embodiment, a first gradient pulse is determined for the first motion state, and a second gradient pulse is determined for the second motion state based on the first B0 field map and the second B0 field map (e.g., by the system control unit of the magnetic resonance apparatus). During performance of the magnetic resonance measurement, the first gradient pulse is switched when the patient is in the first motion state, and/or the second gradient pulse is switched when the patient is in the at least one second motion state (e.g., by a gradient coil unit of the magnetic resonance unit). This does not provide that the first gradient pulse or the second gradient pulse is to be switched whenever the patient is in the first motion state or the second motion state, respectively.

A gradient pulse may be composed of a plurality of partial gradient-pulses; in this case, for example, each partial gradient-pulse may be switched by a gradient coil of the gradient coil unit. For example, the gradient coil unit may include three gradient coils, where, for example, a first of the three gradient coils may switch a magnetic field gradient in an x-direction, a second of the three gradient coils may switch a magnetic field gradient in a y-direction, and a third of the three gradient coils may switch a magnetic field gradient in a z-direction. The x-direction, the y-direction, and the z-direction may form an orthogonal system. By switching the partial gradient-pulses simultaneously, it is possible, for example, by superposition of the magnetic field gradients in the x-, y- and z-directions, to switch a resultant magnetic field gradient in any spatial direction.

The at least one first gradient pulse and the at least one second gradient pulse usually depend on the magnetic resonance sequence used (e.g., on a position of the volume elements to be captured). For example, the at least one first gradient pulse and the at least one second gradient pulse may be taken from a stored library of the system controller and adjusted using parameters. A calculation or an optimization method based on the fields to be achieved and using the Biot-Savart law may also be provided. It is also possible here to take into account dynamic effects such as eddy currents in the magnetic resonance apparatus. The result, for example, is a specified variation over time of an electric current through gradient coils of the gradient coil unit.

During performance of the magnetic resonance measurement, the determined at least one first gradient pulse and/or at least one second gradient pulse may be converted, (e.g., by a gradient control unit) into corresponding currents through gradient coils of a gradient coil unit so as to be able to produce the desired gradient fields.

In one embodiment, the determination of the first excitation pulse and/or the second excitation pulse takes into account dynamic effects of the gradient pulses. It is hence possible for dynamic effects of the gradient pulses to be taken into account and corrected in the excitation pulses. It is thereby possible to improve the quality of the resultant magnetic resonance images, to reduce the effort for correcting for, or preventing, eddy currents, or to reduce the electromagnetic exposure (SAR) for the patient.

A physiological parameter of the patient may be captured. For example, this may be weight, dimensions, position on the couch, or fat content. In one embodiment, for example, this physiological parameter is entered by an operator at an input unit of the magnetic resonance apparatus. It is also possible, however, that the parameter is determined automatically using one or more sensors (e.g., a camera).

This parameter may be taken into account in determining the first excitation pulse and/or the second excitation pulse. For example, the field strength and the permeability, which vary as a result of body weight and composition of the body, may be incorporated in the Bloch equations. The result of the optimization method hence then depends on the physiological parameter.

The first excitation pulse and the second excitation pulse may be transmitted by parallel transmission using a plurality of transmit coils. The parallel transmission may include, for example, simultaneous emission of partial excitation-pulses, with each partial excitation-pulse transmitted by one of the transmit coils. The radiofrequency antenna unit of the magnetic resonance apparatus may have a plurality of transmit coils (e.g., an array of transmit coils).

The magnetic resonance apparatus may have a plurality of transmit channels in order to drive the plurality of transmit coils. An output of a radiofrequency antenna control unit, at which output an excitation signal (e.g., partial excitation signal) corresponding to an excitation pulse may be provided for feeding a transmit coil of the radiofrequency antenna unit, may be regarded as, for example, a transmit channel. The excitation signals (e.g., partial excitation signals) of the transmit channels may differ, for example, in amplitude, spectral power distribution, and/or phase. An excitation pulse may also be described, for example, by a vector including a plurality of excitation signals (e.g., partial excitation signals) for individual transmit channels, which, given time-coordinated emission via the transmit coils, result in a desired excitation of the nuclear spins in the examination space.

The radiofrequency antenna unit includes, for example, an antenna array having a plurality of transmit coils, where each of the signal outputs is in signal communication with at least one transmit coil in order to produce an alternating magnetic field (e.g., a B1 field). These may be, for example, single elements or a plurality of elements of a birdcage antenna, or a plurality of antenna coils of a local-coil array.

Thus, by transmitting the first excitation pulse and/or the second excitation pulse, a predefined spatial distribution of the excitation as an additional degree of freedom may be achieved through interference of the signals from the plurality of transmit channels via a plurality of transmit elements of the radiofrequency antenna unit. The spatial distribution may be set, for example, by varying the phase and/or amplitude when determining the first excitation pulse and/or the second excitation pulse. It is hence possible to improve the homogeneity of the excitation with even lower SAR exposure.

According to a further embodiment of the method, the first motion state and the second motion state are motion states that recur cyclically (e.g., during the magnetic resonance measurement). For example, the first motion state and the second motion state may be motion states caused by a respiratory motion and/or by a cardiac motion. As a result of the continuous recurrence of the motion states during the magnetic resonance measurement, specific excitation pulses that take account of the current motion state (e.g., the B0 field caused by the current motion state) may be transmitted repeatedly.

According to an embodiment of the method, the first motion state is an inspiration state, and the second motion state is an expiration state.

The inspiration state may be a state in which the patient has inhaled. It is usual in this state for the rib cage of the patient to be raised. The expiration state may be a state in which the patient has exhaled. It is usual in this state for the rib cage of the patient to be lowered. Hence, specific excitation pulses that take account of a respiratory motion of the patient may be determined and transmitted during the magnetic resonance measurement. For example, this may make it possible to achieve reliable fat saturation in the region of the diaphragm.

According to a further embodiment of the method, the first motion state and the second motion state are captured during the acquisition of the at least one first B0 field map and/or the at least one second B0 field map by a sensor unit and/or by a sequence-based method.

A sensor unit may include, for example, one or more sensors. The sensors may be optical and/or acoustic sensors, for example. A sensor unit may include a 3D camera, for example. The sensor unit may be configured, for example, to perform a pilot-tone method as described in US 20180353139 A1 by way of example. For example, such a sensor unit may be used to detect whether the patient is in an inspiration state or an expiration state.

A sequence-based method may be based on a magnetic resonance sequence, for example, that is suitable for capturing motion information. For example, the magnetic resonance sequence may include at least one navigator pulse. A magnetic resonance sequence of this type may also be referred to as a navigator sequence. A navigator sequence may be used, for example, to detect a movement of the diaphragm of the patient. For example, it is thereby possible to capture whether the patient is in an inspiration state or an expiration state.

According to a further embodiment of the method, the acquisition of the at least one first B0 field map and/or the at least one second B0 field map and/or the performance of the magnetic resonance measurement are controlled by motion gating (e.g., respiratory gating) and/or are controlled by motion triggering (e.g., respiratory triggering). The motion gating and/or the motion triggering may be performed by a sensor unit and/or by a sequence-based method.

For example, as a result of the motion gating, only data (e.g., magnetic resonance signals and/or measurement data excited by the first excitation pulse and/or second excitation pulse for creating a B0 field map and/or a B1 field map) that was acquired at a time instant at which the patient was in a defined motion state (e.g., in the first motion state or the second motion state) is used. For example, this data may be assigned subsequently or retrospectively (e.g., after a large amount of data has been acquired) to one of the defined motion states of the patient. This large amount of data may also include data that was acquired at a time instant in which the patient was not in one of the defined motion states. For example, the motion states may be captured by a sensor unit and/or by a sequence-based method.

For example, as a result of the motion triggering, only data (e.g., magnetic resonance signals and/or measurement data excited by the first excitation pulse and/or the second excitation pulse for creating a B0 field map and/or a B1 field map) is acquired when the patient is in a defined motion state (e.g., in the first motion state or the second motion state). For example, the data acquisition is initiated by a trigger event at a defined point of a motion cycle (e.g., of a respiratory cycle). The trigger event may be, for example, attaining a defined motion state (e.g., the first motion state or the second motion state). For example, the trigger event may be captured by a sensor unit and/or by a sequence-based method. Motion triggering, unlike motion gating, may be a solely prospective method.

In addition, a magnetic resonance apparatus that is configured to perform an above-described method for performing a magnetic resonance measurement of a patient. For example, the magnetic resonance apparatus may include a radiofrequency antenna unit for producing an excitation pulse, a gradient coil unit for producing magnetic field gradients, a system control unit for determining an excitation pulse, device(s) for acquiring a B0 field map, and/or device(s) for monitoring a motion state of the patient (e.g., a sensor unit).

The advantages of the magnetic resonance apparatus of the present embodiments are essentially the same as the advantages detailed above for the method for performing a magnetic resonance measurement of a patient. Features mentioned in this connection may also be applied to the magnetic resonance apparatus.

In addition, a computer program product that includes a program and may be loaded directly into a memory of a programmable system control unit of a magnetic resonance apparatus, and has program means (e.g., libraries and auxiliary functions) in order to execute an above-described method for performing a magnetic resonance measurement of a patient using the magnetic resonance apparatus when the computer program product is executed in the system control unit of the magnetic resonance apparatus is provided. The computer program product may include software containing a source code that still needs to be compiled and linked or just needs to be interpreted, or an executable software code that, for execution, only needs to be loaded into the system control unit. The method may be performed quickly, reproducibly, and robustly by the computer program product. The computer program product is configured such that the computer program product may perform the acts of the method using the system control unit. The system control unit may have the necessary specifications such as, for example, a suitable RAM, a suitable graphics card, or a suitable logic unit in order to be able to perform the respective method acts efficiently.

The computer program product is stored, for example, on a computer-readable medium or on a network or server, from where the computer program product may be loaded into the processor of a local system control unit. The processor may be connected directly to the magnetic resonance apparatus or may form part of the magnetic resonance apparatus. In addition, control data of the computer program product may be stored on an electronically readable data storage medium. The control data in the electronically readable data storage medium may be configured such that the control data performs a method according to the present embodiments when the data storage medium is used in a system control unit of a magnetic resonance apparatus. Examples of electronically readable data storage media are a DVD, a magnetic tape, or a USB stick, on which electronically readable control data (e.g., software) is stored. When this control data is read from the data storage medium and stored in a system control unit of the magnetic resonance apparatus, all the embodiments according to the present embodiments of the above-described methods may be performed. Hence, the present embodiments may also proceed from the computer-readable medium and/or from the electronically readable data storage medium.

BRIEF DESCRIPTION OF THE DRAWINGS

Corresponding parts are denoted by the same reference signs in all the figures, in which.

DETAILED DESCRIPTION

Figure 1:
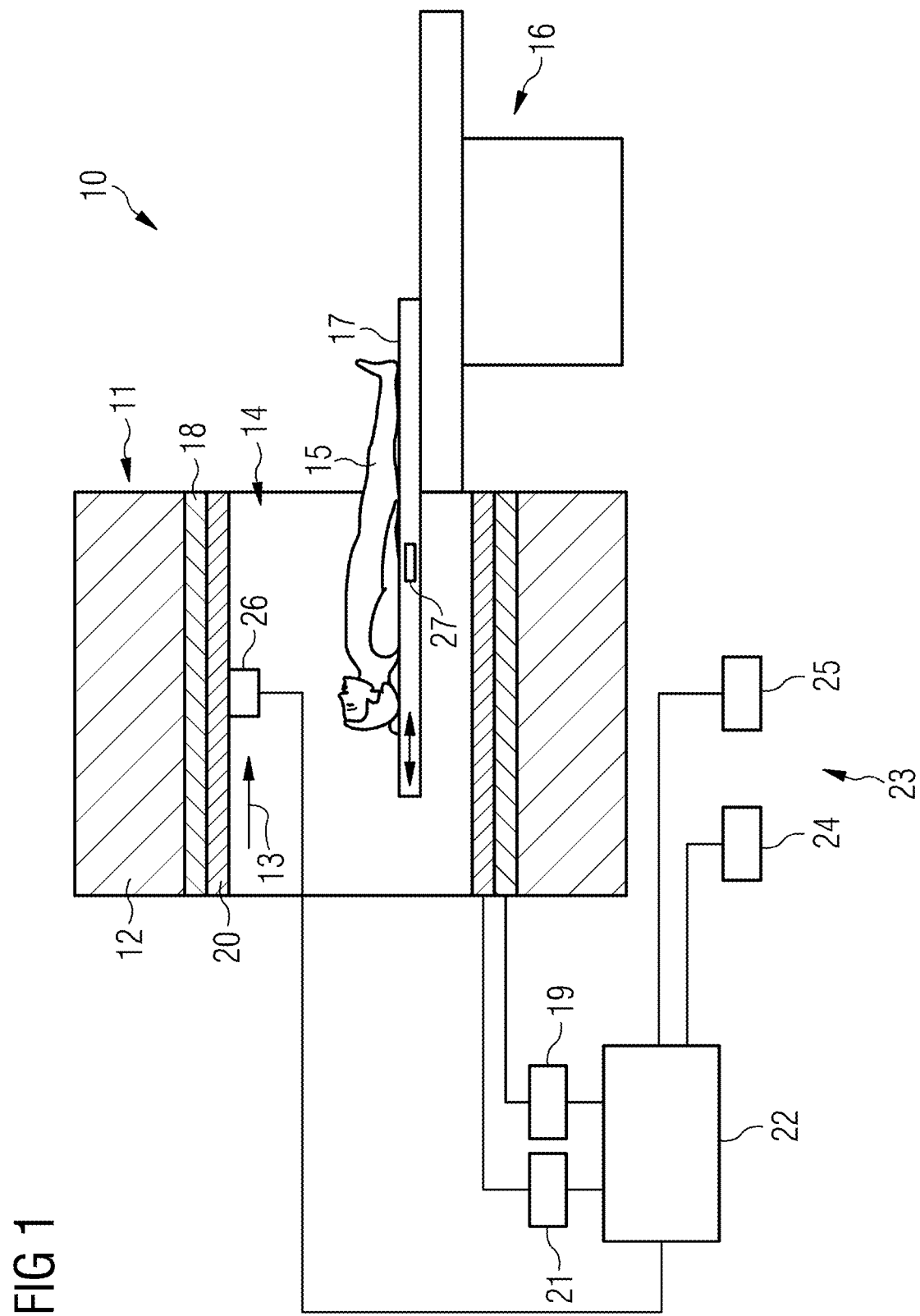
FIG. 1 shows one embodiment of a magnetic resonance apparatus for performing a method for performing a magnetic resonance measurement of a patient.

FIG. 1 shows schematically a possible magnetic resonance apparatus 10. The magnetic resonance apparatus 10 includes a magnet unit 11 that has a main magnet 12 for producing a powerful main magnetic field 13 that, for example, is constant over time. The magnetic resonance apparatus 10 also includes a patient placement zone 14 for accommodating a patient 15. In the present exemplary embodiment, the patient placement zone 14 is shaped as a cylinder and is enclosed in a circumferential direction cylindrically by the magnet unit 11. In principle, however, the patient placement zone 14 may have a different design. The patient 15 may be moved into the patient placement zone 14 by a patient positioning apparatus 16 of the magnetic resonance apparatus 10. The patient positioning apparatus 16 has, for this purpose, a patient couch 17 configured to be able to move inside the patient placement zone 14.

The magnet unit 11 further has a gradient coil unit 18 for generating magnetic field gradients that are used for spatial encoding during imaging. The gradient coil unit 18 is controlled by a gradient control unit 19 of the magnetic resonance apparatus 10. The magnet unit 11 also includes a radiofrequency antenna unit 20 that, in the present exemplary embodiment, is configured as a body coil that is fixedly integrated in the magnetic resonance apparatus 10. The radiofrequency antenna unit 20 is controlled by a radiofrequency antenna control unit 21 of the magnetic resonance apparatus 10 and radiates radiofrequency excitation pulses into an examination space that is largely formed by a patient placement zone 14 of the magnetic resonance apparatus 10. Excitation of nuclear spins in the patient 15 is thereby established in the main magnetic field 13 produced by the main magnet 12. Magnetic resonance signals are produced by relaxation of the excited nuclear spins. The radiofrequency antenna unit 20 is configured to receive the magnetic resonance signals. Magnetic resonance apparatuses often also have as part of the radiofrequency antenna unit 20 one or more local coils (not shown here) that are suitable, for example, for receiving the magnetic resonance signals because the one or more local coils may be mounted close to the patient 15. In one embodiment, especially when the main magnetic field 13 has a particularly high field strength, for example, one or more local coils (e.g., local-coil arrays) also perform the transmission of the excitation pulses.

The magnetic resonance apparatus 10 has a system control unit 22 for controlling the main magnet 12, the gradient control unit 19, and the radiofrequency antenna control unit 21. The system control unit 22 centrally controls the magnetic resonance apparatus 10 (e.g., performing a magnetic resonance measurement, such as performing a predefined magnetic resonance sequence). In addition, the system control unit 22 includes an analysis unit (not presented in further detail) for analyzing the magnetic resonance signals captured during the magnetic resonance measurement. In addition, the magnetic resonance apparatus 10 includes a user interface 23 that is connected to the system control unit 22. Control data such as imaging parameters, for example, and reconstructed magnetic resonance images may be displayed to medical personnel on a display unit 24 (e.g., on at least one monitor) of the user interface 23. In addition, the user interface 23 has an input unit 25 that may be used by the medical operating personnel to enter data and/or parameters during a measurement process.

In this example, the magnetic resonance apparatus 10 also includes a camera 26 that is suitable for capturing and transferring to the system control unit 22 the motion state of the patient 15. The magnetic resonance apparatus 10 also includes in this example a sensor 27 for transmitting a pilot tone. The sensor 27 is arranged here by way of example in the patient table 17. This may allow the motion state of the patient 15 to be captured by a pilot-tone method as described in US 20180353139 A1 by way of example.

Figure 2:
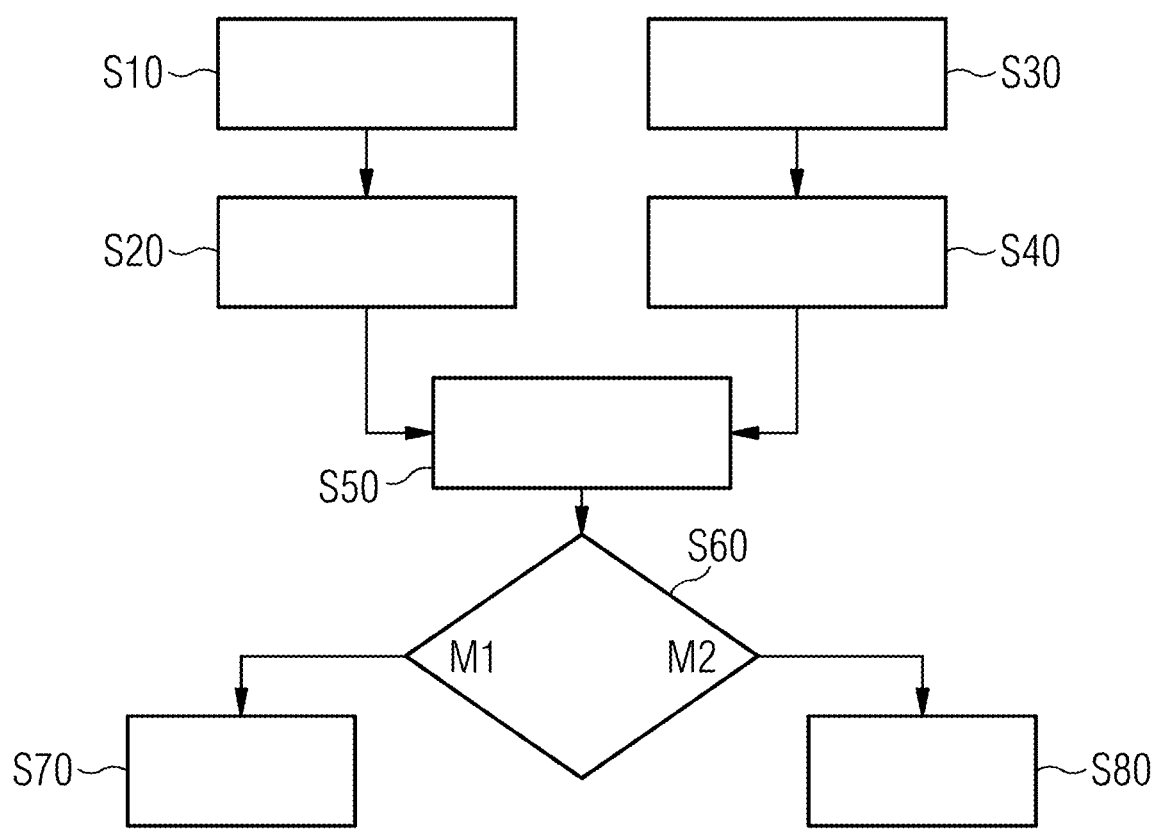
FIG. 2 shows one embodiment of a method for performing a magnetic resonance measurement of a patient using the magnetic resonance apparatus.

FIG. 2 shows schematically a possible method for performing a magnetic resonance measurement of a patient 15 using a magnetic resonance apparatus 10.

In S10, a first B0 field map is provided for a first motion state. For example, the first B0 field map is acquired at one or more first time instants in which the patient 15 is in a first motion state M1 (e.g., an inspiration state). In one embodiment, in S10, a first B1 field map is additionally provided (e.g., acquired) for the first motion state. In S20, a first excitation pulse is determined for the first motion state M1 based on the first B0 field map and possibly also based on the first B1 field map. In one embodiment, in S20, a first gradient pulse is also determined for the first motion state M1 based on the first B0 field map and possibly also based on the first B1 field map.

In S30, a second B0 field map is provided for a second motion state. For example, the second B0 field map is acquired at one or more second time instants in which the patient 15 is in a second motion state M2 (e.g., an expiration state). In one embodiment, in S10, a second B1 field map is additionally provided (e.g., acquired) for the second motion state. In S40, a second excitation pulse is determined for the second motion state M2 based on the second B0 field map and possibly also based on the second B1 field map. In one embodiment, in S40, a second gradient pulse is also determined for the second motion state M2 based on the second B0 field map and possibly also based on the second B1 field map.

In S50, a magnetic resonance measurement is started. During performance of the magnetic resonance measurement, the motion state of the patient is monitored in S60.

When the patient 15 is in the first motion state M1, in S70, the radiofrequency antenna unit 20 transmits the first excitation pulse, which was determined in S20, into the patient placement zone 14. For example, the radiofrequency antenna unit 20 may include a plurality of transmit coils so that the first excitation pulse and the second excitation pulse may also be transmitted by parallel transmission using a plurality of transmit coils (e.g., using a pTx pulse). In one embodiment, in S70, the gradient coil unit 18 also switches the second gradient pulse, which was possibly determined in S20.

When the patient 15 is in the second motion state M2, in S80, the radiofrequency antenna unit 20 transmits the first excitation pulse, which was determined in S40, into the patient placement zone 14. In one embodiment, in S70, the gradient coil unit 18 also switches the second gradient pulse, which was possibly determined in S40.

In the method shown in FIG. 2, an excitation pulse and possibly also a gradient pulse are determined and transmitted or switched only for each of two motion states of the patient 15. It is also possible that a further excitation pulse and possibly also a further gradient pulse are determined and transmitted or switched for each of further motion states of the patient. Then, accordingly, also B0 field maps, and possibly also B1 field maps, may then be acquired for these motion states.

Figure 3:
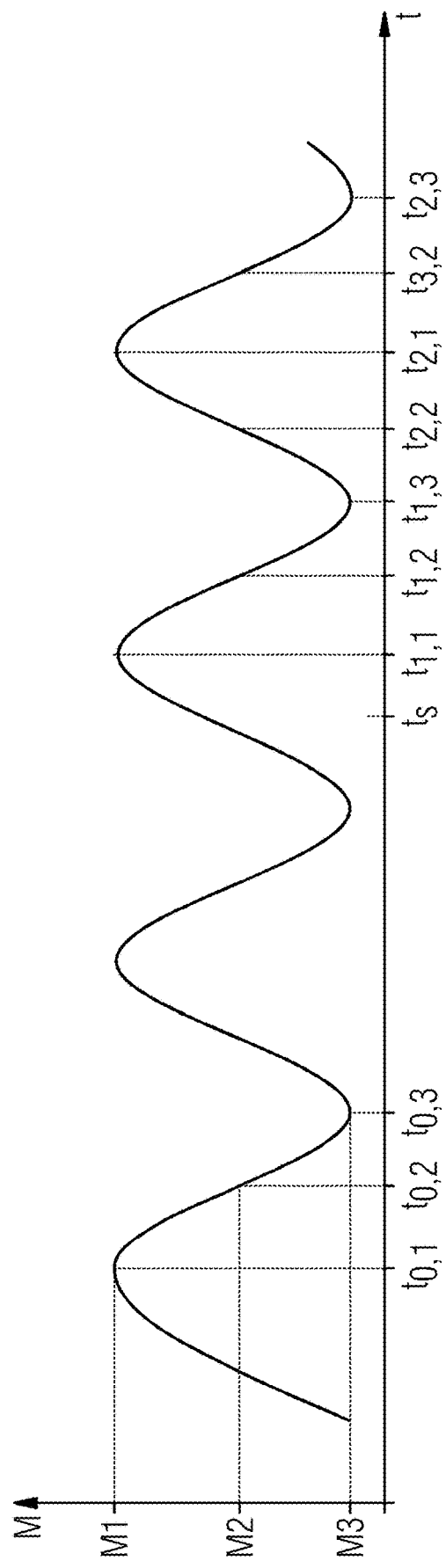
FIG. 3 shows possible timing of various method acts.

FIG. 3 is used to explain in greater detail possible timing of the method, according to which an excitation pulse and possibly also a gradient pulse are determined and transmitted or switched for each of three motion states of the patient. The axis t shows the time, while the axis M represents the motion state of the patient 15. For example, M may be a measure of the height of the rib cage of the patient 15, which is captured, for example, by the sensor unit 26 (e.g., a 3D camera). The curve shown in FIG. 3 represents by way of example a respiratory motion of the patient 15.

At each of the time instants $t_{0,1}$, $t_{0,2}$, and $t_{0,3}$, a B0 map and, optionally, a B1 map of the object to be measured (e.g., of the patient 15) or image region are acquired (cf. S10 and S30 in FIG. 2). At time instant $t_{0,1}$, the patient is in the motion state M1 in which the patient 15 has inhaled, for example, and therefore, his rib cage is raised. During the exhalation, the patient 15 occupies at the time instant $t_{0,2}$ the motion state M2. When the patient has completed the exhalation process, the patient occupies at the time instant $t_{0,3}$ the motion state M3.

In one embodiment, each B0 field map (e.g., complete B0 field map) is acquired not just at one single time instant, as shown in FIG. 3, but at a plurality of time instants in which the patient recurrently occupies the associated motion state; in this case, a portion of the B0 field map may be recorded at each of these multiple time instants. For example, the capture of the motion states or the acquisition of the B0 or B1 maps may be performed by f motion triggering or motion gating. For example, one or more sensor units (e.g., the camera 26 and/or the pilot-tone transmitter 27) together with the radiofrequency antenna unit 20 may be used, or sequence-based methods may be used, to control the motion triggering or motion gating.

Then excitation pulses are calculated based on the recorded field maps; cf. S20 and S40 in FIG. 2 These excitation pulses may be spectrally selective excitation pulses that are each configured, for example, to achieve saturation of the nuclear spins as the excitation to be achieved. The excitation pulses may be, for example, adjusted dynamic saturation pulses (dFX), and therefore one dFX pulse is calculated for each of the motion states M1, M2, M3. Thus, a first excitation pulse is calculated for the motion state M1, a second excitation pulse is calculated for the motion state M2, and a third excitation pulse is calculated for the motion state M3.

When inhaling and exhaling, the patient 15 occupies cyclically recurring motion states that also occur again later during the magnetic resonance measurement. For example, an inspiration state and an expiration state are repeatedly occupied in this case. The magnetic resonance measurement starts at the time instant $t_s$.

The motion state is also monitored during the measurement (cf. S60 in FIG. 2). This monitoring may be performed in the same way in which the motion state is performed at the time instants $t_{0,1}$, $t_{0,2}$, and $t_{0,3}$ (e.g., during acquisition of the B0 maps, and, if applicable, of the B1 maps). If the patient now has one of the motion states M1, M2, or M3, an excitation pulse adjusted for the motion state, and, if applicable, also a gradient pulse adjusted for the motion state are applied (cf. S70 and S80 in FIG. 2). Therefore, in this example, the first excitation pulse is sent at the time instants $t_{1,1}$ and $t_{2,1}$, the second excitation pulse is sent at the time instants $t_{1,2}$, $t_{2,2}$ and $t_{3,2}$, and the third excitation pulse is sent at the time instants $t_{1,3}$ and $t_{2,3}$ and $t_{3,2}$ (e.g., a dynamic saturation pulse in each case). These pulses may be transmitted repeatedly over the subsequent course of the magnetic resonance measurement.

Figure 4:
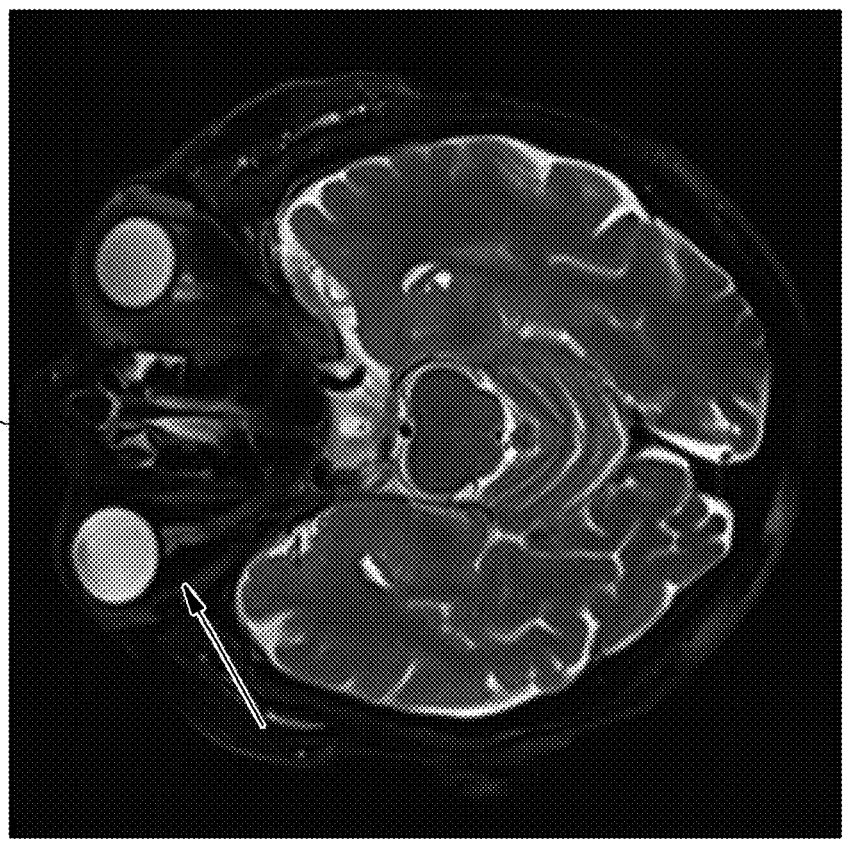
FIG. 4 shows an exemplary comparison of reconstructed magnetic resonance images using, and without using, an embodiment of a method.
Figure 4:
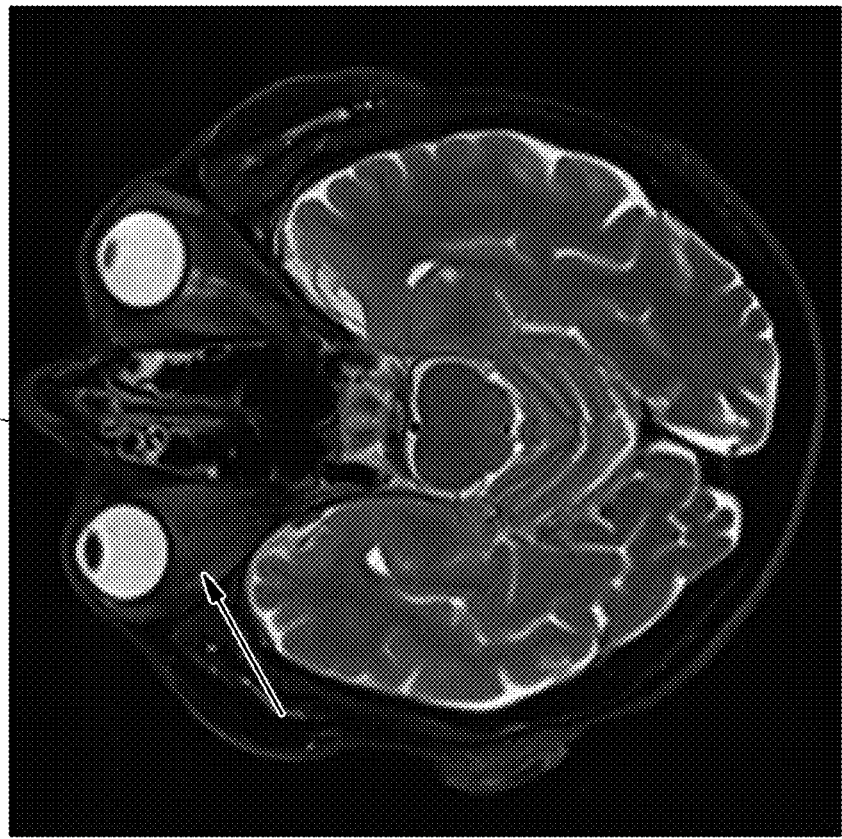

FIG. 4 shows a magnetic resonance image I1, for which an excitation pulse adjusted specifically for the motion state has not been used, and a magnetic resonance image I2, for which an excitation pulse adjusted specifically for the motion state according to the above description has been used. Both magnetic resonance images, for example, show eye sockets; in the magnetic resonance image I1, however, the conventional spectral fat saturation has partly failed, whereas in the magnetic resonance image I2, homogeneous fat saturation may be achieved by dFX pulses. This is shown in the region indicated by the arrows.

By virtue of the proposed method, it may be achieved that even when the patient is moving, at each spatial point, a correct target frequency, if applicable, shifted with respect to the B0 field, is saturated; this is done by taking into account, according to the motion state of the patient 15, B0-field deviations in the image region, for example, induced by the system (e.g., magnet, eddy currents) or by the patient (e.g., anatomy, such as in the neck). The improved spectral saturation of substances such as fat or water may hence be achieved.

The method of one or more of the present embodiments takes into account, for example, the state of the B0 distribution at the time instant of the fat saturation, and hence, may improve especially those magnetic resonance measurements that are affected by movement. Examples are movements in the area surrounding respiratory and cardiac motion, for which, for example, in the region of the diaphragm, reliable fat saturation is not possible using current techniques. Since the B0 distribution is altered by this motion and may look significantly different in expiration or inspiration, for example, this problem may be solved at least partially according to the method (e.g., dFX pulses). For example, it is thereby possible to improve abdominal imaging in which, for example, measurements are performed under free breathing or even when breath is held.

The methods described in detail above and the magnetic resonance apparatus are merely exemplary embodiments that may be modified by a person skilled in the art in many ways without departing from the scope of the invention. In addition, the use of the indefinite article "a" or "an" does not rule out the possibility of there also being more than one of the features concerned. Likewise, the term "unit" does not exclude the possibility that the components in question consist of a plurality of interacting sub-components that may also be spatially distributed if applicable.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for performing a magnetic resonance measurement of a patient using a magnetic resonance apparatus, the magnetic resonance apparatus including a radiofrequency antenna unit for producing an excitation pulse, the method comprising:
   providing a first B0 field map for a first motion state of the patient, and at least one further B0 field map for at least one further motion state of the patient;
   determining a first excitation pulse for the first motion state and at least one further excitation pulse for the at least one further motion state based on the first B0 field map and the at least one further B0 field map; and
   performing the magnetic resonance measurement, during which a motion state of the patient is monitored,
   wherein the radiofrequency antenna unit transmits the first excitation pulse when the patient is in the first motion state,
   wherein the radiofrequency antenna unit transmits the at least one further excitation pulse when the patient is in the at least one further motion state,
   wherein the magnetic resonance apparatus further includes a gradient coil unit operable to produce magnetic field gradients, wherein a first gradient pulse for the first motion state and at least one further gradient pulse for the at least one further motion state are determined based on the first B0 field map and a second B0 field map, the at least one further gradient pulse being different than the first gradient pulse,
   wherein the gradient coil unit applies the first gradient pulse when the patient is in the first motion state, wherein the gradient coil unit applies the at least one further gradient pulse when the patient is in the at least one further motion state, and wherein each of the first excitation pulse and the at least one further excitation pulse is a spectrally selective excitation pulse that is configured to achieve saturation of nuclear spins of a first bond type as the excitation to be achieved, such that flip angles of the first bond type and a second bond type are altered by different amounts.

2. The method of claim 1, wherein the first B0 field map, the at least one further B0 field map, or the first B0 field map and the at least one further B0 field map are produced using acquired measurement data, simulation, or the acquired measurement data and the simulation.

3. The method of claim 1, further comprising:
acquiring the first B0 field map at at least one first time instant, and the at least one further B0 field map at at least one further time instant,
wherein the patient is in the first motion state at the at least one first time instant, and the patient is in the at least one further motion state at the at least one further time instant.

4. The method of claim 1, further comprising:
providing a first B1 field map for the first motion state of the patient, and at least one further B1 field map for at least one further motion state of the patient; and
determining the first excitation pulse and a second excitation pulse also based on the first B1 field map and the at least one further B1 field map.

5. The method of claim 1, wherein the first excitation pulse and the at least one further excitation pulse are transmitted by parallel transmission using a plurality of transmit coils.

6. The method of claim 1, wherein the first motion state and the at least one further motion state are cyclically recurring motion states.

7. The method of claim 6, wherein the first motion state is an inspiration state, and
wherein the at least one further motion state is an expiration state.

8. The method of claim 1, wherein the first motion state and the at least one further motion state are captured during acquisition of the first B0 field map, the at least one further B0 field map, or the first B0 field map and the at least one further B0 field map using a sensor unit, a sequence-based method, or the sensor unit and the sequence-based method.

9. The method of claim 1, wherein acquisition of the first B0 field map, acquisition of the at least one further B0 field map, performance of the magnetic resonance measurement, or any combination thereof is controlled by motion gating, motion triggering, or motion gating and motion triggering.

10. The method of claim 9, wherein the motion gating, the motion triggering, or the motion gating and the motion triggering are performed by a sensor unit, a sequence-based method, or the sensor unit and the sequence-based method.

11. The method of claim 1, further comprising capturing a physiological parameter of the patient,
wherein the captured physiological parameter is taken into account in the determining of the first excitation pulse, the determining of the at least one further excitation pulse, or the determining of the first excitation pulse and the at least one further excitation pulse.

12. A magnetic resonance apparatus that is configured to perform a magnetic resonance measurement of a patient, the magnetic resonance apparatus comprising:

a gradient coil unit operable to produce magnetic field gradients;
a radiofrequency antenna unit configured to produce an excitation pulse; and
a processor configured to:
provide a first B0 field map for a first motion state of the patient, and at least one further B0 field map for at least one further motion state of the patient;
determine a first excitation pulse for the first motion state and at least one further excitation pulse for the at least one further motion state based on the first B0 field map and the at least one further B0 field map; and
perform the magnetic resonance measurement, during which a motion state of the patient is monitored,
wherein the radiofrequency antenna unit is configured to transmit the first excitation pulse when the patient is in the first motion state,
wherein the radiofrequency antenna unit is configured to transmit the at least one further excitation pulse when the patient is in the at least one further motion state,
wherein the processor is further configured to determine a first gradient pulse for the first motion state and at least one further gradient pulse for the at least one further motion state based on the first B0 field map and a second B0 field map, the at least one further gradient pulse being different than the first gradient pulse,
wherein the gradient coil unit is configured to:
apply the first gradient pulse when the patient is in the first motion state; and
apply the at least one further gradient pulse when the patient is in the at least one further motion state, and
wherein each of the first excitation pulse and the at least one further excitation pulse is a spectrally selective excitation pulse that is configured to achieve saturation of nuclear spins of a first bond type as the excitation to be achieved, such that flip angles of the first bond type and a second bond type are altered by different amounts.

13. In a non-transitory computer-readable storage medium that stores instructions executable by one or more processors to perform a magnetic resonance measurement of a patient using a magnetic resonance apparatus, the magnetic resonance apparatus including a radiofrequency antenna unit for producing an excitation pulse, the instructions comprising:
providing a first B0 field map for a first motion state of the patient, and at least one further B0 field map for at least one further motion state of the patient;
determining a first excitation pulse for the first motion state and at least one further excitation pulse for the at least one further motion state based on the first B0 field map and the at least one further B0 field map; and
performing the magnetic resonance measurement, during which a motion state of the patient is monitored,
wherein the radiofrequency antenna unit transmits the first excitation pulse when the patient is in the first motion state,
wherein the radiofrequency antenna unit transmits the at least one further excitation pulse when the patient is in the at least one further motion state,
wherein the magnetic resonance apparatus further includes a gradient coil unit operable to produce magnetic field gradients,
wherein a first gradient pulse for the first motion state and at least one further gradient pulse for the at least one further motion state are determined based on the first B0 field map and a second B0 field map, the at least one further gradient pulse being different than the first gradient pulse, wherein the gradient coil unit applies the first gradient pulse when the patient is in the first motion state, wherein the gradient coil unit applies the at least one further gradient pulse when the patient is in the at least one further motion state, and wherein each of the first excitation pulse and the at least one further excitation pulse is a spectrally selective excitation pulse that is configured to achieve saturation of nuclear spins of a first bond type as the excitation to be achieved, such that flip angles of the first bond type and a second bond type are altered by different amounts.

14. The non-transitory computer-readable storage medium of claim 13, wherein the first B0 field map, the at least one further B0 field map, or the first B0 field map and the at least one further B0 field map are produced using acquired measurement data, simulation, or the acquired measurement data and the simulation.

15. The non-transitory computer-readable storage medium of claim 13, wherein the instructions further comprise:

acquiring the first B0 field map at at least one first time instant, and the at least one further B0 field map at at least one further time instant, wherein the patient is in the first motion state at the at least one first time instant, and the patient is in the at least one further motion state at the at least one further time instant.

16. The non-transitory computer-readable storage medium of claim 13, wherein the instructions further comprise:

providing a first B1 field map for the first motion state of the patient, and at least one further B1 field map for at least one further motion state of the patient; and determining the first excitation pulse and a second excitation pulse also based on the first B1 field map and the at least one further B1 field map.

* * * * *